(12) United States Patent
Zellner

(10) Patent No.: US 6,528,081 B1
(45) Date of Patent: Mar. 4, 2003

(54) NASAL SPRAY LIQUID

(76) Inventor: Gerhard Zellner, Im Poschengrund 11, D-83435 Bad Reichenhall (DE)

( * ) Notice: Subject to any disclaimer, the term of this patent is extended or adjusted under 35 U.S.C. 154(b) by 0 days.

(21) Appl. No.: 09/358,498

(22) Filed: Jul. 21, 1999

(51) Int. Cl.⁷ .................................................. A61F 13/00
(52) U.S. Cl. ....................................... 424/434; 424/422
(58) Field of Search ................................ 424/422, 434

(56) References Cited

U.S. PATENT DOCUMENTS

| | | | |
|---|---|---|---|
| 4,581,226 A | | 4/1986 | Dillon |
| 4,668,513 A | * | 5/1987 | Reichert ..................... 424/94 |
| 5,281,580 A | * | 1/1994 | Yamamoto et al. ........... 514/12 |
| 5,760,085 A | * | 6/1998 | Beck et al. .................. 514/613 |
| 5,804,211 A | * | 9/1998 | Robertson et al. .......... 424/434 |
| 5,882,866 A | * | 3/1999 | Keene .......................... 435/6 |

FOREIGN PATENT DOCUMENTS

| | | |
|---|---|---|
| EP | 0 053 754 | 6/1982 |
| GB | 2 267 434 | 12/1993 |

OTHER PUBLICATIONS

J. Niquet et al, Phys Rehab Kur Med 6 (1996) 186–189.

* cited by examiner

*Primary Examiner*—Thurman K. Page
*Assistant Examiner*—S. Tran
(74) *Attorney, Agent, or Firm*—Flynn, Thiel, Boutell & Tanis, P.C.

(57) ABSTRACT

The spray liquid of a nasal spray is formed by a hyperosmotically adjusted water saline solution with a common salt content of 1 to 4% by weight. It furthermore contains various essential oils.

6 Claims, No Drawings

NASAL SPRAY LIQUID

The invention relates to a spray liquid for a nasal spray made of a watery saline solution.

Common nasal sprays contain, almost obligatorily, vessel-constricting substances for reducing the swelling of the mucous membrane, often also cortisone. While cortisone has known negative side effects, the medications, which simply reduce the swelling of the mucous membrane, can result in regeneration breakdowns of the nasal mucous membrane and physical dependency.

It is also known to use an isotonic saline solution as a nasal spray liquid (Brochure "Phinomer" of the Novartis Consumer Health GmbH, 81366 Muenchen, Edition 4/97; U.S. Pat. No. 4,518,226A) or nasal sprays based on essential oils (EP 00 53 754 A1). However, nasal sprays made of isotonic saline solutions and nasal sprays based on essential oils do not result in substantial improvement in the patients with restricted nasal breathing or an incrusted nose, not even during long-term therapy.

It is known from GB 22 67 434 A to use sodium chloride in a hypotonic concentration against all forms of nausea. Furthermore, an inhalation therapy has been carried out with patients having obstructive respiratory duct illnesses using hyperosmotic saline solutions in comparison to physiological saline solutions or without inhalation treatment. The therapeutic effectiveness of an inhalation therapy with hyperosmotic saline solutions could not be proven (J. Niquet et al, Phys Rehab Kur Med 6 (1996) 186–189).

The purpose of the invention is to make a nasal spray available, which, without any negative side effects, enables an effective, soothing nasal care, whereby at the same time a prevention against respiratory duct illness occurs.

This is achieved according to the invention in such a manner that the spray liquid is formed by a watery saline solution with a common salt content of at least 1% by weight. This means that the spray liquid has a hyperphysiological or hyperosmolaric common salt concentration. With this, the swelling of the nasal mucous membrane is reduced by the removal of fluid. In addition, the watery saline solution results in the dissolving of crusts and stuck mucus. Besides this mucus or secretion and crust dissolving action, the nasal spray of the invention stimulates the ciliary kinetics, which causes the finest particles, like dust, soot, pollen and other aerogeneous allergens, in particular, animal epitheliens, mold fungus spores, mite extracts, latex particles, etc., also bacteria and viruses, to be removed quicker through the small cilia.

The upper limit of the common salt concentration of the nasal spray of the invention lies at approximately 4% by weight. Undesired side effects can occur starting with this concentration. Normally the common salt concentration lies between 2 and 3% by weight.

A diluted natural salt solution and mine salt solution are used preferably as the saline solution. The saturated salt solution, which has a common salt content of approximately 26%, can for this purpose be diluted with water, for example, to ten times. However, it can also be a different saline solution, for example a sea salt solution.

The natural salt solution can, for example, also be a solution from the underground springs of the Reichenhall Saltern. A natural salt solution is an excellent natural healing remedy for persons with illnesses of the respiratory ducts. It is significantly richer than common salt, namely, it contains, besides sodium chloride, small amounts of many valuable minerals and trace elements.

The spray liquid created according to the invention by using a natural salt solution is thus an original palaeontological thalasso theraputicum absolutely free of toxic agents for the care of the upper respiratory passages and for the prevention of illnesses of the respiratory ducts.

Besides common salt or a natural salt solution, the nasal spray of the invention may contain a Ringer lactate solution and essential oils, whereby an alkaline buffered Ringer lactate solution is preferred.

Essential oils represent characteristically scented, essential herbal active agents, which support today's often overly stressed immune system through their disinfecting and strong germ-killing action. They have antiseptic, vegetatively regulating, mood-lifting and creativity-stimulating characteristics. They increase the willingness to learn, stimulate creativity and introduce a happy note into concentrative and physical labor, which, as has been proven, results in a reduction of the error quota. The essential oils in the nasal spray of the invention also result in clarification processes in the case of emotional conflicts. Besides mood-lifting, anxiety-resolving and pain-relieving characteristics, it is possible for the essential oils in the nasal spray to activate hidden energy sources without any hypnotic risks and to show consciousness-increasing effects.

Lemon oil, eucalyptus oil, balm oil, mint oil, camphor, aniseed oil, rosemary oil and sage oil are preferably used as essential oils. The effects of these essential oils are characterized as follows:

Lemon oil: germ-killing, immunizing, stimulative, concentration-stimulating, happiness-conveying Eucalyptus oil: antiseptic, expectorant, stimulates the intellect Balm oil: hypersensitivity-damping, vegetatively balancing Mint oil: antiseptic, refreshing, expectorant, concentration-stimulating Camphor: stimulates breathing, antiseptic Aniseed oil: stops sneezing, cramping relief Rosemary oil: toning, memory-improving Sage oil: antiseptic, roborizing The concentration of the essential oils is preferably, in total, 1 mg to 50 mg, in particular 5 mg to 15 mg per 10 ml, whereby preferably 0.5 mg to 10 mg, in particular, 1 mg to 5 mg lemon oil, preferably 0.5 mg to 10 mg, in particular, 1 mg to 5 mg eucalyptus oil, preferably 0.05 mg to 5 mg, in particular, 0.1 mg to 0.3 mg balm oil, preferably 0.1 mg to 10 mg, in particular, 0.1 mg to 3 mg mint oil, preferably 0.1 mg to 10 mg, in particular, 0.1 mg to 3 mg camphor, preferably 0.01 mg to 5 mg, in particular, 0.01 mg to 0.5 mg aniseed oil.

preferably 0.01 mg to 5 mg, in particular, 0.01 mg to 0.5 mg rosemary oil, and preferably 0.01 mg to 5 mg, in particular, 0.01 mg to 0.5 mg sage oil, per 10 ml are contained in the nasal spray of the invention.

The nasal spray of the invention is used two times a day with one spray application per nostril under normal circumstances for improving the cleaning and moisturizing of the nasal mucous membrane. This accomplishes an improved well-being and, in an enjoyable manner, a lasting preventative care with respect to illnesses of the respiratory ducts.

The use can at the start of a cold be increased, for example, to five to six spray applications per nostril during the course of a day. When nasal breathing is hindered or temporarily blocked, for example, due to an increase in air-polluting concentrations within the scope of summer smog in large cities, for example the so-called sick-building syndrome, the MCS (multiple chemical sensitivity) syndrome or to crust formation caused by drying, particularly in the winter months, an increased dosage of, for example, three to four spray applications per nostril per day may also be necessary.

The nasal spray of the invention provides general stimulation during a normal workday and at home. It results in an increase in concentration and is suitable as an accident prophylaxis prior and during longer travels in the car. It can also be utilized to optimize the intellectual performance, for example, prior to exams or testing situations.

The nasal spray of the invention is preferably utilized as a pump spray without a propellant gas and does not contain any preservatives. It does not primarily have the rank of a medication, but offers the possibility for soothing nasal care and uncomplicated natural preventative health care.

What is claimed is:

1. A spray liquid for a nasal spray for reducing the swelling of nasal mucous membranes, in which the improvement comprises said spray liquid comprising a hyperosmotically adjusted saline solution having a salt content of from 3 to 4 wt. %.

2. A spray liquid for a nasal spray for reducing the swelling of nasal mucous membranes, in which the improvement comprises said spray liquid consisting essentially of a hyperosmotically adjusted saline solution having a salt content of from 3 to 4 wt. %, 1 to 50 mg in total, based on 10 ml of the spray liquid, of at least one essential oil selected from the group consisting of lemon oil, eucalyptus oil, balm oil, mint oil, camphor, aniseed oil, rosemary oil and sage oil and a Ringer lactate solution.

3. The spray liquid according to claim 1, wherein the saline solution is formed by a diluted natural salt solution or a mine salt solution.

4. The spray liquid according to claim 1, wherein it additionally contains at least one essential oil.

5. The spray liquid according to claim 4, wherein the essential oil is at least one oil selected from the group consisting of lemon oil, eucalyptus oil, balm oil, mint oil, camphor, aniseed oil, rosemary oil and sage oil.

6. The spray liquid according to claim 1, wherein it additionally contains a Ringer lactate solution.

\* \* \* \* \*